US009288996B2

(12) United States Patent
Jabs et al.

(10) Patent No.: US 9,288,996 B2
(45) Date of Patent: Mar. 22, 2016

(54) FUNGICIDAL COMPOSITIONS COMPRISING A PHOSPHATE SOLUBILIZING MICROORGANISM AND A FUNGICIDALLY ACTIVE COMPOUND

(75) Inventors: Thorsten Jabs, Hassloch (DE); Paul Cavell, Limburgerhof (DE); Sarah Dunker, Waldsee (DE); Alexander Wissemeier, Speyer (DE); Egon Haden, Speyer (DE); Tom Wetjen, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/634,890

(22) PCT Filed: Mar. 14, 2011

(86) PCT No.: PCT/IB2011/051058
§ 371 (c)(1), (2), (4) Date: Sep. 14, 2012

(87) PCT Pub. No.: WO2011/114280
PCT Pub. Date: Sep. 22, 2011

(65) Prior Publication Data
US 2013/0017949 A1 Jan. 17, 2013

Related U.S. Application Data

(60) Provisional application No. 61/315,027, filed on Mar. 18, 2010.

(30) Foreign Application Priority Data
Mar. 18, 2010 (EP) .................................... 10156836

(51) Int. Cl.
*A01N 25/26* (2006.01)
*A01N 63/04* (2006.01)

(52) U.S. Cl.
CPC ..................................... *A01N 63/04* (2013.01)

(58) Field of Classification Search
CPC ........................... A01N 63/04; A01N 2300/00
See application file for complete search history.

(56) References Cited

U.S. PATENT DOCUMENTS 3,296,272 A 1/1967 Johnston
3,325,503 A 6/1967 Bimber
4,617,303 A 10/1986 Eicken et al.
RE32,676 E 5/1988 Eicken et al.
4,914,128 A 4/1990 Schirmer et al.
6,265,430 B1 7/2001 Alig et al.
6,277,791 B1 8/2001 Assmann et al.
6,372,692 B1 4/2002 Assmann et al.
6,420,605 B1 7/2002 Eicken et al.
6,458,282 B1 10/2002 Lundbäck
6,509,501 B2 1/2003 Eicken et al.
6,576,631 B1 6/2003 Shibata et al.
6,586,617 B1 7/2003 Tabuchi et al.
6,624,183 B2 9/2003 Wachendorff-Neumann et al.
6,632,771 B1 10/2003 Maekawa et al.
6,642,181 B2 11/2003 Assmann et al.
6,680,402 B2 1/2004 Eicken et al.
6,872,729 B2 3/2005 Shibata et al.
6,875,783 B2 4/2005 Assmann et al.
7,098,227 B2 8/2006 Dunkel et al.
7,115,593 B2 10/2006 Wachendorff-Neumann et al.
7,157,481 B2 1/2007 Assmann et al.
7,208,510 B2 4/2007 Wachendorff-Neumann et al.
7,307,165 B2 12/2007 Tabuchi et al.
7,608,563 B2 10/2009 Tsukamoto et al.
7,696,355 B2 4/2010 Assmann et al.
7,816,526 B2 10/2010 Tanaka et al.
7,956,009 B2 6/2011 Wachendorff-Neumann et al.
7,964,531 B2 6/2011 Tsukamoto et al.
8,008,232 B2 8/2011 Gewehr et al.
2004/0023938 A1 2/2004 Tabuchi et al.
2004/0023966 A1 2/2004 Shibata et al.
2005/0101639 A1* 5/2005 Ammermann et al. ....... 514/345
2007/0167463 A1 7/2007 Blasco et al.
2007/0173408 A1 7/2007 Blasco et al.
2008/0108686 A1 5/2008 Gewehr et al.
2008/0153707 A1 6/2008 Gewehr et al.
2008/0262000 A1 10/2008 Schafer et al.
2009/0036509 A1 2/2009 Gewehr et al.
2009/0118346 A1 5/2009 Dunkel et al.
2010/0160163 A1 6/2010 Tanaka et al.

FOREIGN PATENT DOCUMENTS

CN 1524949 9/2004
DE 196 50 197 6/1998
DE 100 21 412 6/2001
DE 10 2005 009 458 9/2006
EP 0 141 317 5/1985
EP 0 152 031 8/1985
EP 0 226 917 7/1987
EP 0 243 970 11/1987
EP 0 256 503 2/1988
EP 0 428 941 5/1991
EP 0 532 022 3/1993
EP 1 028 125 8/2000
EP 1 035 122 9/2000

(Continued)

OTHER PUBLICATIONS

Gulden RH, and JK Vessey. 2000. Penicillium bilaii inoculation increases root-hair production in field pea. Can. J. Plant Sci.; 80: 801-804.*

(Continued)

*Primary Examiner* — Johann R Richter
*Assistant Examiner* — David Browe
(74) *Attorney, Agent, or Firm* — Brinks Gilson & Lione

(57) ABSTRACT

The present invention relates to a composition, comprising a microorganism of species *Penicillium bilaji* and at least one compound (II) in a synergistically effective amount.

17 Claims, No Drawings

(56) References Cited

FOREIGN PATENT DOCUMENTS

| | | |
|---|---|---|
| EP | 1 122 244 | 8/2001 |
| EP | 1 201 648 | 5/2002 |
| JP | 2002316902 | 10/2002 |
| WO | WO 95/08521 | 3/1995 |
| WO | WO 95/17806 | 7/1995 |
| WO | WO 98/46608 | 10/1998 |
| WO | WO 99/14187 | 3/1999 |
| WO | WO 99/24413 | 5/1999 |
| WO | WO 99/27783 | 6/1999 |
| WO | WO 00/29404 | 5/2000 |
| WO | WO 00/46148 | 8/2000 |
| WO | WO 00/65913 | 11/2000 |
| WO | WO 01/54501 | 8/2001 |
| WO | WO 01/56358 | 8/2001 |
| WO | WO 02/22583 | 3/2002 |
| WO | WO 02/40431 | 5/2002 |
| WO | WO 03/010149 | 2/2003 |
| WO | WO 03/011853 | 2/2003 |
| WO | WO 03/014103 | 2/2003 |
| WO | WO 03/016286 | 2/2003 |
| WO | WO 03/053145 | 7/2003 |
| WO | WO 03/061388 | 7/2003 |
| WO | WO 03/066609 | 8/2003 |
| WO | WO 03/074491 | 9/2003 |
| WO | WO 2004/049804 | 6/2004 |
| WO | WO 2004/083193 | 9/2004 |
| WO | WO 2005/063721 | 7/2005 |
| WO | WO 2005/087772 | 9/2005 |
| WO | WO 2005/087773 | 9/2005 |
| WO | WO 2005/120234 | 12/2005 |
| WO | WO 2005/123689 | 12/2005 |
| WO | WO 2005/123690 | 12/2005 |
| WO | WO 2006/012739 | 2/2006 |
| WO | WO 2006/015866 | 2/2006 |
| WO | WO 2006/087325 | 8/2006 |
| WO | WO 2006/087343 | 8/2006 |
| WO | WO 2007/082098 | 7/2007 |
| WO | WO 2007/090624 | 8/2007 |
| WO | WO 2009/060012 | 5/2009 |
| WO | WO 2009/091557 | 7/2009 |

OTHER PUBLICATIONS

Newsham KK, AH Fitter, and AR Watkinson. 1995. Multi-functionality and biodiversity in arbuscular mycorrhizas. Trends Ecol. Evol.; 10(10): 407-411.*

Anonymous. JUMPSTART wettable powder. Novozymes "Labels/MSDS" sheet [online]; 2008; downloaded as a PDF link from <URL http://www.bioag.novozymes.com/en/products/australia/jumpstart/pages/default.aspx> on Mar. 20, 2015, 3 pages.*

Burton et al., "Survival of *Penicillium bilaiae* inoculated on canola seed treated with Vitavax RS and Extender", Biol. Fertil. Soils, vol. 42, pp. 54-59, 2005.

Goos et al., "*Penicillium bilaji* and phosphorus fertilization effects on the growth, development, yield and common root rot severity of spring wheat", Fertilizer Research, vol. 39, pp. 97-103, 1994.

Leggett et al., "Development of guidelines for the use of PROVIDE™ on wheat and canola", Plant nutrition—from genetic engineering to field practice, pp. 375-378, 1993.

Mills et al., "Determination of Selective Action of Fungicides on the Microflora of Barley Seed", Can. J. Plant Sci., vol. 48, pp. 587-594, 1968.

International Search Report, PCT/IB2011/051058, completed Apr. 11, 2012.

International Preliminary Report on Patentability, PCT/IB2011/051058, issued Sep. 18, 2012.

* cited by examiner

FUNGICIDAL COMPOSITIONS COMPRISING A PHOSPHATE SOLUBILIZING MICROORGANISM AND A FUNGICIDALLY ACTIVE COMPOUND

This application is a National Stage application of International Application No. PCT/IB2011/051058, filed Mar. 14, 2011, which claims the benefit of U.S. Provisional Application No. 61/315,027, filed Mar. 18, 2010, the entire contents of which are hereby incorporated herein by reference. This application also claims priority under 35 U.S.C. §119 to European Patent Application No. 10156836.8, filed Mar. 18, 2010, the entire contents of which is hereby incorporated herein by reference.

The present invention relates to fungicidal compositions for controlling phytopathogenic harmful fungi comprising, as active components, 1) a microorganism (I) of species *Penicillium bilaji; and*

2) at least one compound (II), selected from the active compound groups A) to F):

A) strobilurins azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl)-phenyl)-2-methoxyimino-N-methyl-acetamide;

B) carboxamides carboxanilides: benalaxyl, benalaxyl-M, benodanil, bixafen, boscalid, carboxin, fenfuram, fenhexamid, flutolanil, fluxapyroxad, furametpyr, isopyrazam, isotianil, kiralaxyl, mepronil, metalaxyl, metalaxyl-M (mefenoxam), ofurace, oxadixyl, oxycarboxin, penflufen, penthiopyrad, sedaxane, tecloftalam, thifluzamide, tiadinil, 2-amino-4-methyl-thiazole-5-carboxanilide, N-(4'-trifluoromethylthiobiphenyl-2-yl)-3-difluoromethyl-1-methyl-1H-pyrazole-4-carboxamide and N-(2-(1,3,3-trimethylbutyl)-phenyl)-1,3-dimethyl-5-fluoro-1H-pyrazole-4-carboxamide;

carboxylic morpholides: dimethomorph, flumorph, pyrimorph;

benzoic acid amides: flumetover, fluopicolide, fluopyram, zoxamide;

other carboxamides: carpropamid, dicyclomet, mandiproamid, oxytetracyclin, silthiofam and N-(6-methoxy-pyridin-3-yl) cyclopropanecarboxylic acid amide;

C) azoles triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole;

imidazoles: cyazofamid, imazalil, pefurazoate, prochloraz, triflumizol;

D) heterocyclic compounds pyridines: fluazinam, pyrifenox, 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine;

pyrimidines: bupirimate, cyprodinil, diflumetorim, fenarimol, ferimzone, mepanipyrim, nitrapyrin, nuarimol, pyrimethanil;

piperazines: triforine;

pyrroles: fenpiclonil, fludioxonil;

morpholines: aldimorph, dodemorph, dodemorph-acetate, fenpropimorph, tridemorph;

piperidines: fenpropidin;

dicarboximides: fluoroimid, iprodione, procymidone, vinclozolin;

non-aromatic 5-membered heterocycles: famoxadone, fenamidone, flutianil, octhilinone, probenazole, 5-amino-2-isopropyl-3-oxo-4-ortho-tolyl-2,3-dihydro-pyrazole-1-carbothioic acid S-allyl ester;

others: acibenzolar-S-methyl, ametoctradin, amisulbrom, anilazin, blasticidin-S, captafol, captan, chinomethionat, dazomet, debacarb, diclomezine, difenzoquat, difenzoquat-methylsulfate, fenoxanil, Folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole and 5-chloro-7-(4-methylpiperidin-1-yl)-6-(2,4,6-trifluorophenyl)-[1,2,4]triazolo-[1,5-a]pyrimidine;

E) other active substances guanidines: guanidine, dodine, dodine free base, guazatine, guazatine-acetate, iminoctadine, iminoctadine-triacetate, iminoctadine-tris(albesilate);

antibiotics: kasugamycin, kasugamycin hydrochloride-hydrate, streptomycin, polyoxine, validamycin A;

nitrophenyl derivates: binapacryl, dicloran, dinobuton, dinocap, nitrothal-isopropyl, tecnazen, organometal compounds: fentin salts, such as fentin-acetate, fentin chloride or fentin hydroxide;

sulfur-containing heterocyclyl compounds: dithianon, isoprothiolane;

organophosphorus compounds: edifenphos, fosetyl, fosetyl-aluminum, iprobenfos, phosphorus acid and its salts, pyrazophos, tolclofos-methyl;

organochlorine compounds: chlorothalonil, dichlofluanid, dichlorophen, flusulfamide, hexachlorobenzene, pencycuron, pentachlorphenole and its salts, phthalide, quintozene, thiophanate-methyl, tolylfluanid, N-(4-chloro-2-nitro-phenyl)-N-ethyl-4-methyl-benzenesulfonamide;

inorganic active substances: Bordeaux mixture, copper acetate, copper hydroxide, copper oxychloride, basic copper sulfate, sulfur;

F) antifungal biocontrol agents, plant bioactivators: *Ampelomyces quisqualis* (e.g. AQ 10® from Intrachem Bio GmbH & Co. KG, Germany), *Aspergillus flavus* (e.g. AFLAGUARD® from Syngenta, CH), *Aureobasidium pullulans* (e.g. BOTECTOR® from bio-ferm GmbH, Germany), *Bacillus pumilius* (e.g. isolate NRRL-Nr. B-21661 in RHAPSODY®, SERENADE® MAX and SERENADE® ASO from Fa. AgraQuest Inc., USA), *Bacillus subtilis* var. *amyloliquefaciens* FZB24 (e.g. TAEGRO® from Novozyme Biologicals, Inc., USA), *Candida oleophila* I-82 (e.g. ASPIRE® from Ecogen Inc., USA), *Candida saitoana* (e.g. BIO-CURE® (in mixture with lysozyme) and BIOCOAT® from Micro Flo Company, USA (BASF SE) and Arysta), Chitosan (e.g. ARMOUR-ZEN from BotriZen Ltd., NZ), *Clonostachys rosea* f. *catenulata*, also named *Gliocladium catenulatum* (e.g. isolate J1446: PRESTOP® from Verdera, Finland), *Coniothyrium minitans* (e.g. CONTANS® from Prophyta, Germany), *Cryphonectria parasitica* (e.g. *Endothia parasitica* from CNICM, France), *Cryptococcus albidus* (e.g. YIELD PLUS® from Anchor Bio-Technologies, South Africa), *Fusarium oxysporum* (e.g. BIOFOX® from S.I.A.P.A., Italy, FUSACLEAN® from Natural Plant Protection, France), *Metschnikowia fructicola* (e.g. SHEMER® from Agrogreen, Israel), *Microdochium dimerum* (e.g. ANTIBOT® from Agrauxine, France), *Phlebiopsis gigantea* (e.g. ROTSOP® from Verdera, Finland), *Pseudozyma flocculosa* (e.g. SPORODEX® from Plant Products Co. Ltd., Canada), *Pythium oligandrum* DV74 (e.g. POLYVERSUM® from Remeslo SSRO, Biopreparaty, Czech Rep.), *Reynoutria sachlinensis* (e.g. REGALIA® from Marrone BioInnovations, USA), *Talaromyces flavus* V117b (e.g. PROTUS® from Prophyta, Germany), *Trichoderma asperellum* SKT-1 (e.g. ECO-HOPE® from Kumiai Chemical Industry Co., Ltd., Japan), *T. atroviride* LC52 (e.g. SENTINEL® from Agrimm Technologies Ltd, NZ), *T. harzianum* T-22 (e.g. PLANTSHIELD® der Firma BioWorks Inc., USA), *T. harzianum* TH 35 (e.g. ROOT PRO® from Mycontrol Ltd., Israel), *T. harzianum* T-39 (e.g. TRICHODEX® and TRICHODERMA 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ricerca, Italy), *T. polysporum* and *T. harzianum* (e.g. BINAB® from BINAB Bio-Innovation AB, Sweden), *T. stromaticum* (e.g. TRICOVAB® from C.E.P.L.A.C., Brazil), *T. virens* GL-21 (e.g. SOILGARD® from Certis LLC, USA), *T. viride* (e.g. TRIECO® from Ecosense Labs. (India) Pvt. Ltd., Indien, BIO-CURE® F from T. Stanes & Co. Ltd., Indien), *T. viride* TV1 (e.g. *T. viride* TV1 from Agribiotec srl, Italy), *Ulocladium oudemansii* HRU3 (e.g. BOTRY-ZEN® from Botry-Zen Ltd, NZ);

in a synergistically effective amount.

Moreover, the invention relates to a method for controlling harmful fungi using a fungicidal composition of components 1) and 2), to the use of a component 1) with a component 2) for preparing such compositions, and also to agents and seed treated with such compositions.

Isolates of the fungal species *Penicillium bilaji* (also named *P. bilaiae* or *P. bilaii*) which are effective in phosphate solubilization and in enhancement of crop yield due to improved fertilization are known from Fertilizer Research 39, 97-103, 1994. In a field trial, inoculation with *Penicillium bilaji* has not been found to influence the disease severity of common root rot of spring wheat (Fertilizer Research 39, 97-103, 1994). Further use of this fungal microorganism in nutritional ingredients for oral administration to humans and animals has been described in WO 2006/012739.

Suitable formulations of the of species *Penicillium bilajii* are commercially available under the tradenames Jump-Start® from NOVOZYMES Biologicals BioAg, Canada.

The term compounds (II) shall be understood as comprising not only compounds per se but also biological control agents (see group F). The compounds (II) referred to as component 2), their preparation and their activity against harmful fungi is known (cf.: http://www.alanwood.net/pesticides/); these substances are commercially available. The compounds described by IUPAC nomenclature, their preparation and their fungicidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. No. 3,296,272; U.S. Pat. No. 3,325, 503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624).

However, the known compounds (II), in particular at low application rates, are not always entirely satisfactory.

It was an object of the present invention, with a view to reducing the application rates and broadening the activity spectrum of the compounds (II), to provide compositions which, at a reduced total amount of active compounds applied, have improved activity against harmful fungi, in particular for certain indications.

We have accordingly found that this object is achieved by the compositions, of components 1) and 2), defined at the outset. Moreover, we have found that simultaneous, that is joint or separate, application of components 1) and 2) or successive application of the components 1) and 2) allows better control of harmful fungi than is possible with the strains, their mutants and the metabolites produced by the strains on the one hand and with the individual compounds (II) on the other hand, alone (synergistic mixtures). By simultaneous, that is joint or separate, application of components 1) and 2), the fungicidal activity is increased in a superadditive manner.

Component 1) embraces not only the isolated, pure cultures of the *Penicillium bilaji*, but also their suspensions in a whole broth culture or as a metabolite-containing supernatant or a purified metabolite obtained from a whole broth culture of the strain. "Whole broth culture" refers to a liquid culture containing both cells and media. "Supernatant" refers to the liquid broth remaining when cells grown in broth are removed by centrifugation, filtration, sedimentation, or other means well known in the art. The term "metabolite" refers to any compound, substance or by product of a fermentation or a microorganism.

Many of the compounds (II) can be present in different crystal modifications, which may differ in biological activity. They also form part of component 2).

Preference is given to compositions of a component 1) with a component 2) wherein component 1) is the product Jump-Start from NOVOZYMES Biologicals BioAg, Canada, comprising *Penicillium bilaji*.

Preference is given to compositions of a component 1) with a component 2) consisting of at least one compound (II) selected from the group of A) strobilurins more preferably selected from pyraclostrobin, trifloxystrobin, azoxystrobin and fluoxastrobin, in particular pyraclostrobin.

Preference is also given to compositions of a component 1) with a component 2) consisting of at least one compound (II) selected from the group of B) carboxamides. Among the group of B) boscalid, isopyrazam, metalaxyl, metalaxyl-M, penflufen, dimethomorph, fluopyram, penthiopyrad, sedaxane, bixafen and fluxapyroxad are preferred. More preferably, compounds (II) are selected from bixafen, boscalid, fluxapyroxad, penflufen, penthiopyrad and sedaxane, even more preferably from fluxapyroxad and penflufen. Preference is also given compounds II selected from metalxyl and metalaxyl-M. Preference is also given to compounds (II) selected from fluopyram and dimethomorph, in particular dimethomorph.

Preference is given to compositions of a component 1) with a component 2) consisting of at least one compound (II) selected from the group of C) azoles, preferably selected from cyproconazole, difenoconazole, diniconazole, epoxiconazole, fluquinconazole, metconazole, ipconazole, imazalil, tebuconazole, triticonazole, prothioconazole, and prochloraz, more preferably from prothioconazole, tebuconazole, triticonazole and prochloraz.

Preference is furthermore also given to compositions of a component 1) with a component 2) consisting of at least one compound (II) selected from the group of D) heterocyclic compounds. Among the D) heterocyclic compounds, fludioxonil, cyprodinil, pyrimethanil and iprodione are preferred, in particular fludioxonil.

Preference is furthermore also given to compositions of a component 1) with a component 2) consisting of at least one compound (II) selected from the group of E) other fungicides. Among the E) other fungicides, guazatine, phosphorus acid and its salts and thiophanate-methyl are preferred.

Preference is also given to compositions of a component 1) with a component 2) consisting of at least one compound (II) selected from the group of F) biocontrol agents, in particular *Bacillus pumilis.*

Particular preference is given to compositions of a component 1) with a component 2) consisting of at least one compound (II) selected from groups A), C), D) and E), whereas each of C), D) and E) may consist of all members or the preferred embodiments.

Preference is also given to three-component compositions comprising a component 1), wherein component 2) consists of two of the compounds (II) mentioned above, more preferably these two compounds (II) are selected from groups A), C), D) and E), whereas each of A), C), D) and E) may consist of all members or the preferred embodiments.

Particular preference is given to compositions of a component 1) with a component 2) consisting of two compounds (II) one selected from group A) and the other being selected from group C), in particular the two compounds (II) are pyraclostrobin and triticonazole.

Particular preference is given to compositions of a component 1) with a component 2) consisting of two compounds (II) both selected from group C), in particular the two compounds (II) are prochloraz and triticonazole.

The compositions according to the invention, respectively, are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

The compositions according to the invention are particularly important in the control of a multitude of phytopathogenic fungi on various cultivated plants, such as cereals, e. g. wheat, rye, barley, triticale, oats or rice; beet, e. g. sugar beet or fodder beet; fruits, such as pomes, stone fruits or soft fruits, e. g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called Stevia); natural rubber plants or ornamental and forestry plants, such as flowers, shrubs, broad-leaved trees or evergreens, e. g. conifers; and on the plant propagation material, such as seeds, and the crop material of these plants.

Preferably, compositions are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with compounds I and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://www.bio.org/speeches/pubs/er/agri_products.asp). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e. g. by glycosylation or polymer additions such as prenylated, acetylated or farnesylated moieties or PEG moieties.

The compositions according to the invention are particularly suitable for controlling the following plant diseases:

*Albugo* spp. (white rust) on ornamentals, vegetables (e. g. *A. candida*) and sunflowers (e. g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e. g. *A. solani* or *A. alternata*), tomatoes (e. g. *A. solani* or *A. alternata*) and wheat; *Aphanomyces* spp. on sugar beets and vegetables; *Ascochyta* spp. on cereals and vegetables, e. g. *A. tritici* (anthracnose) on wheat and *A. hordei* on barley; *Bipolaris* and *Drechslera* spp. (teleomorph: *Cochliobolus* spp.), e. g. Southern leaf blight (*D. maydis*) or Northern leaf blight (*B. zeicola*) on corn, e. g. spot blotch (*B. sorokiniana*) on cereals and e.g.

*B. oryzae* on rice and turfs; *Blumeria* (formerly *Erysiphe*) *graminis* (powdery mildew) on cereals (e. g. on wheat or barley); *Botrytis cinerea* (teleomorph: *Botryotinia fuckeliana*: grey mold) on fruits and berries (e. g. strawberries), vegetables (e. g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e. g. *C. ulmi* (Dutch elm disease) on elms; *Cercospora* spp. (*Cercospora* leaf spots) on corn (e.g. Gray leaf spot: *C. zeae-maydis*), rice, sugar beets (e. g. *C. beticola*), sugar cane, vegetables, coffee, soybeans (e. g. *C. sojina* or *C. kikuchii*) and rice; *Cladosporium* spp. on tomatoes (e. g. *C. fulvum*: leaf mold) and cereals, e. g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e. g. *C. sativus*, anamorph: *B. sorokiniana*) and rice (e. g. *C. miyabeanus*, anamorph: *H. oryzae*); *Colletotrichum* (teleomorph: *Glomerella*) spp. (anthracnose) on cotton (e. g. *C. gossypii*), corn (e. g. *C. graminicola*: Anthracnose stalk rot), soft fruits, potatoes (e. g. *C. coccodes*: black dot), beans (e. g. *C. lindemuthianum*) and soybeans (e. g. *C. truncatum* or *C. gloeosporioides*); *Corticium* spp., e. g. *C. sasakii* (sheath blight) on rice; *Corynespora cassiicola* (leaf spots) on soybeans and ornamentals; *Cycloconium* spp., e. g. *C. oleaginum* on olive trees; *Cylindrocarpon* spp. (e. g. fruit tree canker or young vine decline, teleomorph: *Nectria* or *Neonectria* spp.) on fruit trees, vines (e. g. *C. liriodendri*, teleomorph: *Neonectria liriodendri*: Black Foot Disease) and ornamentals; *Dematophora* (teleomorph: *Rosellinia*) necatrix (root and stem rot) on soybeans; *Diaporthe* spp., e. g. *D. phaseolorum* (damping off) on soybeans; *Drechslera* (syn. *Helminthosporium*, teleomorph: *Pyrenophora*) spp. on corn, cereals, such as barley (e. g. *D. teres*, net blotch) and wheat (e. g. *D. tritici-repentis*: tan spot), rice and turf; Esca (dieback, apoplexy) on vines, caused by *Formitiporia* (syn. *Phellinus*) *punctata, F. mediterranea, Phaeomoniella chlamydospora* (earlier *Phaeoacremonium chlamydosporum*), *Phaeoacremonium aleophilum* and/or *Botryosphaeria obtusa; Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e. g. *E. pisi*), such as cucurbits (e. g. *E. cichoracearum*), cabbages, rape (e. g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e. g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e. g. wheat or barley), *F. oxysporum* on tomatoes, *F. solani* on soybeans and *F. verticillioides* on corn; *Gaeumannomyces graminis* (take-all) on cereals (e. g. wheat or barley) and corn; *Gibberella* spp. on cereals (e. g. *G. zeae*) and rice (e. g. *G. fujikuroi*: Bakanae disease); *Glomerella cingulata* on vines, pome fruits and other plants and *G. gossypii* on cotton; Grainstaining complex on rice; *Guignardia bidwellii* (black rot) on vines; *Gymnosporangium* spp. on rosaceous plants and junipers, e. g. *G. sabinae* (rust) on pears; *Helminthosporium* spp. (syn. *Drechslera*, teleomorph: *Cochliobolus*) on corn, cereals and rice; *Hemileia* spp., e. g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e. g. wheat or barley); *Microsphaera diffusa* (powdery mildew) on soybeans; *Monilinia* spp., e. g. *M. laxa, M. fructicola* and *M. fructigena* (bloom and twig blight, brown rot) on stone fruits and other rosaceous plants; *Mycosphaerella* spp. on cereals, bananas, soft fruits and ground nuts, such as e. g. *M. graminicola* (anamorph: *Septoria tritici, Septoria* blotch) on wheat or *M. fijiensis* (black Sigatoka disease) on bananas; *Peronospora* spp. (downy mildew) on cabbage (e. g. *P. brassicae*), rape (e. g. *P. parasitica*), onions (e. g. *P. destructor*), tobacco (*P. tabacina*) and soybeans (e. g. *P. manshurica*); *Phakopsora pachyrhizi* and *P. meibomiae* (soybean rust) on soybeans; *Phialophora* spp. e. g. on vines (e. g. *P. tracheiphila* and *P. tetraspora*) and soybeans (e. g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e. g. *P. viticola*: can and leaf spot) and soybeans (e. g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e. g. *P. capsici*), soybeans (e. g. *P. megasperma*, syn. *P. sojae*), potatoes and tomatoes (e. g. *P. infestans*: late blight) and broad-leaved trees (e. g. *P. ramorum*: sudden oak death); *Plasmodiophora brassicae* (club root) on cabbage, rape, radish and other plants; *Plasmopara* spp., e. g. *P. viticola* (grapevine downy mildew) on vines and *P. halstedii* on sunflowers; *Podosphaera* spp. (powdery mildew) on rosaceous plants, hop, pome and soft fruits, e. g. *P. leucotricha* on apples; *Polymyxa* spp., e. g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e. g. wheat or barley; *Pseudoperonospora* (downy mildew) on various plants, e. g. *P. cubensis* on cucurbits or *P. humili* on hop; *Pseudopezicula tracheiphila* (red fire disease or, rotbrenner', anamorph: *Phialophora*) on vines; *Puccinia* spp. (rusts) on various plants, e. g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye, *P. kuehnii* (orange rust) on sugar cane and *P. asparagi* on asparagus; *Pyrenophora* (anamorph: *Drechslera*) *triticirepentis* (tan spot) on wheat or *P. teres* (net blotch) on barley; *Pyricularia* spp., e. g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e. g. *P. ultimum* or *P. aphanidermatum*); *Ramularia* spp., e. g. *R. collo-cygni* (*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e. g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e. g. *S. sclerotiorum*) and soybeans (e. g. *S. rolfsii* or *S. sclerotiorum*); *Septoria* spp. on various plants, e. g. *S. glycines* (brown spot) on soybeans, *S. tritici* (*Septoria* blotch) on wheat and *S.* (syn. *Stagonospora*) *nodorum* (*Stagonospora* blotch) on cereals; *Uncinula* (syn. *Erysiphe*) *necator* (powdery mildew, anamorph: *Oidium tuckeri*) on vines; *Setospaeria* spp. (leaf blight) on corn (e. g. *S. turcicum*, syn. *Helminthosporiuth turcicum*) and turf; *Sphacelotheca* spp. (smut) on corn, (e. g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e. g. *S. nodorum* (*Stagonospora* blotch, teleomorph: *Leptosphaeria* [syn. *Phaeosphaeria] nodorum*) on wheat; *Synchytrium endobioticum* on potatoes (potato wart disease); *Taphrina* spp., e. g. *T. deformans* (leaf curl disease) on peaches and *T. pruni* (plum pocket) on plums; *Thielaviopsis* spp. (black root rot) on tobacco, pome fruits, vegetables, soybeans and cotton, e. g. *T. basicola* (syn. *Chalara elegans*); *Tilletia* spp. (common bunt or stinking smut) on cereals, such as e. g. *T. tritici* (syn. *T. caries*, wheat bunt) and *T. controversa* (dwarf bunt) on wheat; *Typhula incarnata* (grey snow mold) on barley or wheat; *Urocystis* spp., e. g. *U. occulta* (stem smut) on rye; *Uromyces* spp. (rust) on vegetables, such as beans (e. g. *U. appendiculatus*, syn. *U. phaseoli*) and sugar beets (e. g. *U. betae*); *Ustllago* spp. (loose smut) on cereals (e. g. *U. nuda* and *U. avaenae*), corn (e. g. *U. maydis*: corn smut) and sugar cane; *Venturia* spp. (scab) on apples (e. g. *V. inaequalis*) and pears; and *Verticillium* spp. (wilt) on various plants, such as fruits and ornamentals, vines, soft fruits, vegetables and field crops, e. g. *V. dahliae* on strawberries, rape, potatoes and tomatoes.

The compounds I and compositions thereof, respectively, are also suitable for controlling harmful fungi in the protection of stored products or harvest and in the protection of materials. The term "protection of materials" is to be understood to denote the protection of technical and non-living materials, such as adhesives, glues, wood, paper and paperboard, textiles, leather, paint dispersions, plastics, coiling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans, Scierophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichorma* spp., *Alternaria* spp., *Paecilomyces* spp. and Zygomycetes such as *Mucor* spp., and in addition in the protection of stored products and harvest the following yeast fungi are worthy of note: *Candida* spp. and *Saccharomyces cerevisae.*

The compositions may be used for improving the health of a plant. The invention also relates to a method for improving plant health by treating a plant, its propagation material and/or the locus where the plant is growing or is to grow with an effective amount of the compositions according to the invention.

The term "plant health" is to be understood to denote a condition of the plant and/or its products which is determined by several indicators alone or in combination with each other such as yield (e. g. increased biomass and/or increased content of valuable ingredients), plant vigor (e. g. improved plant growth and/or greener leaves ("greening effect")), quality (e. g. improved content or composition of certain ingredients) and tolerante to abiotic and/or biotic stress. The above identified indicators for the health condition of a plant may be interdependent or may result from each other.

The microorganisms (I) and the compounds (II) are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with a composition according to the invention prophylactically either at or before planting or transplanting.

The invention also relates to fungicidal compositions comprising a solvent or solid carrier and at least one microorganism (I) and one compound (II) and to the use for controlling harmful fungi.

A fungicidal composition comprises a fungicidally effective amount of a composition according to the invention. The term "effective amount" denotes an amount of the compositions, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific composition used.

The compounds (II) and the microorganism (I) can be converted into customary types of compositions, e. g. solutions, emulsions, suspensions, dusts, powders, pastes and granules. The composition type depends on the particular intended purpose; in each case, it should ensure a fine and uniform distribution of the compound according to the invention.

Examples for composition types are suspensions (SC, OD, FS), emulsifiable concentrates (EC), emulsions (EW, EO, ES), pastes, pastilles, wettable powders or dusts (WP, SP, SS, WS, DP, DS) or granules (GR, FG, GG, MG), which can be water-soluble or wettable, as well as gel formulations for the treatment of plant propagation materials such as seeds (GF).

Usually the composition types (e. g. SC, OD, FS, EC, WG, SG, WP, SP, SS, WS, GF) are employed diluted. Composition types such as DP, DS, GR, FG, GG and MG are usually used undiluted.

The compositions are prepared in a known manner (cf. U.S. Pat. No. 3,060,084, EP-A 707 445 (for liquid concentrates), Browning: "Agglomeration", Chemical Engineering, Dec. 4, 1967, 147-48, Perry's Chemical Engineer's Handbook, 4th Ed., McGraw-Hill, New York, 1963, S. 8-57 and ff. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman: Weed Control as a Science (J. Wiley & Sons, New York, 1961), Hance et al.: Weed Control Handbook (8th Ed., Blackwell Scientific, Oxford, 1989) and Mollet, H. and Grubemann, A.: Formulation technology (Wiley VCH Verlag, Weinheim, 2001).

The compositions may also comprise auxiliaries which are customary in compositions. The auxiliaries used depend on the particular application form and active substance, respectively.

Examples for suitable auxiliaries are solvents, solid carriers, dispersants or emulsifiers (such as further solubilizers, protective colloids, surfactants and adhesion agents), organic and anorganic thickeners, bactericides, anti-freezing agents, anti-foaming agents, if appropriate colorants and tackifiers or binders (e. g. for seed treatment formulations).

Suitable solvents are water, organic solvents such as mineral oil fractions of medium to high boiling point, such as kerosene or diesel oil, furthermore coal tar oils and oils of vegetable or animal origin, aliphatic, cyclic and aromatic hydrocarbons, e. g. toluene, xylene, paraffin, tetrahydronaphthalene, alkylated naphthalenes or their derivatives, alcohols such as methanol, ethanol, propanol, butanol and cyclohexanol, glycols, ketones such as cyclohexanone and gamma-butyrolactone, fatty acid dimethylamides, fatty acids and fatty acid esters and strongly polar solvents, e. g. amines such as N-methylpyrrolidone.

Solid carriers are mineral earths such as silicates, silica gels, talc, kaolins, limestone, lime, chalk, bole, loess, clays, dolomite, diatomaceous earth, calcium sulfate, magnesium sulfate, magnesium oxide, ground synthetic materials, fertilizers, such as, e. g., ammonium sulfate, ammonium phosphate, ammonium nitrate, ureas, and products of vegetable origin, such as cereal meal, tree bark meal, wood meal and nutshell meal, cellulose powders and other solid carriers.

Suitable surfactants (adjuvants, wtters, tackifiers, dispersants or emulsifiers) are alkali metal, alkaline earth metal and ammonium salts of aromatic sulfonic acids, such as ligninsoulfonic acid (Borresperse® types, Borregard, Norway) phenolsulfonic acid, naphthalenesulfonic acid (Morwet® types, Akzo Nobel, U.S.A.), dibutylnaphthalene-sulfonic acid (Nekal® types, BASF, Germany), and fatty acids, alkylsulfonates, alkylarylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formaldehyde, polyoxy-ethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and proteins, denatured proteins, polysaccharides (e. g. methylcellulose), hydrophobically modified starches, polyvinyl alcohols (Mowiol® types, Clariant, Switzerland), polycarboxylates (Sokolan® types, BASF, Germany), polyalkoxylates, polyvinylamines (Lupasol® types, BASF, Germany), polyvinylpyrrolidone and the copolymers therof.

Examples for thickeners (i. e. compounds that impart a modified flowability to compositions, i. e. high viscosity under static conditions and low viscosity during agitation) are polysaccharides and organic and anorganic clays such as Xanthan gum (Kelzan®, CP Kelco, U.S.A.), Rhodopol® 23 (Rhodia, France), Veegum® (R.T. Vanderbilt, U.S.A.) or Attaclay® (Engelhard Corp., NJ, USA).

Bactericides may be added for preservation and stabilization of the composition. Examples for suitable bactericides are those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie).

Examples for suitable anti-freezing agents are ethylene glycol, propylene glycol, urea and glycerin.

Examples for anti-foaming agents are silicone emulsions (such as e. g. Silikon® SRE, Wacker, Germany or Rhodorsil®, Rhodia, France), long chain alcohols, fatty acids, salts of fatty acids, fluoroorganic compounds and mixtures thereof.

Suitable colorants are pigments of low water solubility and water-soluble dyes. Examples to be mentioned and the designations rhodamin B, C. I. pigment red 112, C. I. solvent red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples for tackifiers or binders are polyvinylpyrrolidons, polyvinylacetates, polyvinyl alcohols and cellulose ethers (Tylose®, Shin-Etsu, Japan).

Powders, materials for spreading and dusts can be prepared by mixing or concomitantly grinding the compounds I and, if appropriate, further active substances, with at least one solid carrier.

Granules, e. g. coated granules, impregnated granules and homogeneous granules, can be prepared by binding the active substances to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, e. g., ammonium sulfate, ammonium phosphate, ammonium nitrate, ureas, and products of vegetable origin, such as cereal meal, tree bark meal, wood meal and nutshell meal, cellulose powders and other solid carriers.

The compositions generally comprise between 0.01 and 95%, preferably between 0.1 and 90%, most preferably between 0.5 and 90%, by weight of compound (II) and micoroorganism (I). The active substances are employed in a purity of from 90% to 100%, preferably from 95% to 100% (according to NMR spectrum).

Water-soluble concentrates (LS), flowable concentrates (FS), powders for dry treatment (DS), water-dispersible powders for slurry treatment (WS), water-soluble powders (SS), emulsions (ES) emulsifiable concentrates (EC) and gels (GF) are usually employed for the purposes of treatment of plant propagation materials, particularly seeds. These compositions can be applied to plant propagation materials, particularly seeds, diluted or undiluted. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying or treating compounds and compositions thereof, respectively, on to plant propagation material, especially seeds, are known in the art, and include dressing, coating, pelleting, dusting, soaking and in-furrow application methods of the propagation material. In a preferred embodiment, the compounds or the compositions thereof, respectively, are applied on to the plant propagation material by a method such that germination is not induced, e. g. by seed dressing, pelleting, coating and dusting.

In a preferred embodiment, a suspension-type (FS) composition is used for seed treatment. Typically, a FS composition may comprise 1-800 g/l of active substance and microorganism, 1-200 g/l Surfactant, 0 to 200 g/l antifreezing agent, 0 to 400 g/l of binder, 0 to 200 g/l of a pigment and up to 1 liter of a solvent, preferably water.

The active substances and the microorganism can be used as such or in the form of their compositions, e. g. in the form of directly sprayable solutions, powders, suspensions, dispersions, emulsions, oil dispersions, pastes, dustable products, materials for spreading, or granules, by means of spraying, atomizing, dusting, spreading, brushing, immersing or pouring. The application forms depend entirely on the intended purposes; it is intended to ensure in each case the finest possible distribution of the active substances according to the invention.

Aqueous application forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active substance concentrations in the ready-to-use preparations can be varied within relatively wide ranges. In general, they are from 0.0001 to 10%, preferably from 0.001 to 1% by weight of active substance.

The active substances may also be used successfully in the ultra-low-volume process (ULV), it being possible to apply compositions comprising over 95% by weight of active substance, or even to apply the active substance without additives.

When employed in plant protection, the amounts of active substances and the microorganism applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha.

In treatment of plant propagation materials such as seeds, e. g. by dusting, coating or drenching seed, amounts of microorganism (I) and compound (II) and the compositions comprising them, are of from 0.01 g to 10 kg per 100 kg of plant propagation material, regularly of from 0.1 to 1000 g, preferably from 1 to 1000 g, more preferably from 1 to 100 g and most preferably from 5 to 100 g, per 100 kg of plant propagation material (preferably seed) are generally required.

When used in the protection of materials or stored products, the amount of active substance applied depends on the kind of application area and on the desired effect. Amounts customarily applied in the protection of materials are, e. g., 0.001 g to 2 kg, preferably 0.005 g to 1 kg, of active substance and microorganism per cubic meter of treated material.

Various types of oils, wetters, adjuvants, herbicides, bactericides, other fungicides and/or pesticides may be added to the microorganism and the active substances or the compositions comprising them, if appropriate not until immediately prior to use (tank mix). These agents can be admixed with the compositions according to the invention in a weight ratio of 1:100 to 100:1, preferably 1:10 to 10:1.

Adjuvants which can be used are in particular organic modified polysiloxanes such as Break Thru S 240®; alcohol alkoxylates such as Atplus 245®, Atplus MBA 1303®, Plurafac LF 300® and Lutensol ON 30®; EO/PO block polymers, e. g. Pluronic RPE 2035® and Genapol B®; alcohol ethoxylates such as Lutensol XP 80®; and dioctyl sulfosuccinate sodium such as Leophen RA®.

The compositions according to the invention can, in the use form as fungicides, also be present together with other active substances, e. g. with herbicides, insecticides, growth regulators, fungicides or else with fertilizers, as pre-mix or, if appropriate, not until immeadiately prior to use (tank mix).

Mixing the binary compositions comprising a microorganism (I) and one further compound (II) in the use form as fungicides with other fungicides results in many cases in an expansion of the fungicidal spectrum of activity being obtained or in a prevention of fungicide resistance development. Furthermore, in many cases, synergistic effects are obtained.

The present invention furthermore relates to compositions comprising a mixture of a microorganism (I) (component 1) and one compound selected from the groups A) to F) (component 2) and at least one further active compound useful for plant protection, e. g. selected from the groups A) to F) (component 3), as described above, and if desired one suitable solvent or solid carrier. Those mixtures are of particular interest, since many of them at the same application rate show higher efficiencies against harmful fungi. Furthermore, combating harmful fungi with a mixture of a microorganism (I) (component 1) and one compound selected from the groups A) to F) (component 2), as described above, is more efficient than combating those fungi with microorganism (I) or individual fungicides from groups A) to F). By applying microorganism (I) together with at least one active substance from groups A) to I) a synergistic effect can be obtained, i.e. more then simple addition of the individual effects is obtained (synergistic mixtures).

In binary mixtures, i.e. compositions according to the invention comprising microorganism (I) (component 1) and one compound (II) (component 2), e. g. one active substance from groups A) to F), the weight ratio of component 1 and component 2 generally depends from the properties of the active substances used, usually it is in the range of from 1:1000 to 1000:1, often in the range of from 1:200 to 200:1, regularly in the range of from 1:50 to 50:1, preferably in the range of from 1:20 to 20:1, more preferably in the range of from 1:10 to 10:1 and in particular in the range of from 1:3 to 3:1.

In ternary mixtures, i.e. compositions according to the invention comprising microorganism (I) (component 1) and a first compound (II) (component 2) and a second compound (II) (component 3), e. g. two active substances from groups A) to F), the weight ratio of component 1 and component 2 depends from the properties of the active substances used, preferably it is in the range of from 1:50 to 50:1 and particularly in the range of from 1:10 to 10:1, and the weight ratio of component 1 and component 3 preferably is in the range of from 1:50 to 50:1 and particularly in the range of from 1:10 to 10:1.

The components can be used individually or already partially or completely mixed with one another to prepare the composition according to the invention. It is also possible for them to be packaged and used further as combination composition such as a kit of parts.

In one embodiment of the invention, the kits may include one or more, including all, components that may be used to prepare a subject composition. E. g., kits may include one or more fungicide component(s) and/or an adjuvant component and/or a insecticide component and/or a growth regulator component and/or a herbicde. One or more of the components may already be combined together or pre-formulated. In those embodiments where more than two components are provided in a kit, the components may already be combined together and as such are packaged in a single container such as a vial, bottle, can, pouch, bag or canister. In other embodiments, two or more components of a kit may be packaged separately, i. e., not pre-formulated. As such, kits may include one or more separate containers such as vials, cans, bottles, pouches, bags or canisters, each container containing a separate component for a composition. In both forms, a component of the kit may be applied separately from or together with the further components or as a component of a combination composition according to the invention for preparing the composition according to the invention.

The user applies the composition according to the invention usually from a predosage device, a knapsack sprayer, a spray tank or a spray plane. Here, the composition is made up with water and/or buffer to the desired application concentration, it being possible, if appropriate, to add further auxiliaries, and the ready-to-use spray liquor or the composition according to the invention is thus obtained. Usually, 50 to 500 liters of the ready-to-use spray liquor are applied per hectare of agricultural useful area, preferably 100 to 400 liters.

According to one embodiment, individual components of the composition according to the invention such as parts of a kit or parts of a binary or ternary mixture may be mixed by the user himself in a spray tank and further auxiliaries may be added, if appropriate (tank mix).

In a further embodiment, either individual components of the composition according to the invention or partially premixed components, e. g. components comprising compounds I and/or active substances from the groups A) to I), may be mixed by the user in a spray tank and further auxiliaries and additives may be added, if appropriate (tank mix).

In a further embodiment, either individual components of the composition according to the invention or partially premixed components, e, g. components comprising compounds I and/or active substances from the groups A) to I), can be applied jointly (e.g. after tankmix) or consecutively.

Preference is also given to mixtures comprising a microorganism (I) (component 1) and at least one active substance selected from the strobilurines of group A) (component 2) and particularly selected from azoxystrobin, dimoxystrobin, fluoxastrobin, kresoxim-methyl, orysastrobin, picoxystrobin, pyraclostrobin and trifloxystrobin.

Preference is also given to mixtures comprising a microorganism (I) (component 1) and at least one active substance selected from the carboxamides of group B) (component 2) and particularly selected from bixafen, boscalid, fluopyram, fluxapyroxad, isopyrazam, penflufen, penthiopyrad, sedaxane, metalaxyl, mefenoxam, ofurace, dimethomorph, flumorph, fluopicolid (picobenzamid), zoxamide, carpropamid and mandipropamid.

Preference is given to mixtures comprising a compound of formula I (component 1) and at least one active substance selected from the azoles of group C) (component 2) and particularly selected from cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole, prochloraz and cyazofamid.

Preference is also given to mixtures comprising a microorganism (I) (component 1) and at least one active substance selected from the heterocyclic compounds of group D) (component 2) and particularly selected from fluazinam, cyprodinil, fenarimol, mepanipyrim, pyrimethanil, triforine, fludioxonil, dodemorph, fenpropimorph, tridemorph, fenpropidin, iprodione, vinclozolin, famoxadone, fenamidone, probenazole, proquinazid, acibenzolar-S-methyl, captafol, folpet, fenoxanil, quinoxyfen and ametoctradin.

Preference is also given to mixtures comprising a microorganism (I) (component 1) and at least one active substance selected from the fungicides given in group E) (component 2) and particularly selected from dithianon, fentin salts, such as fentin acetate, fosetyl, fosetyl-aluminium, $H_3PO_3$ and salts thereof, chlorthalonil, dichlofluanid, thiophanat-methyl, copper acetate, copper hydroxide, copper oxychloride, copper sulfate, sulfur, cymoxanil, metrafenone and spiroxamine.

Preference is also given to mixtures comprising a microorganism (I) (component 1) and at least one active substance selected from the antifungal biocontrol agents given in group F) (component 2) and particularly selected from *Bacillus subtilis* strain NRRL No. B-21661, *Bacillus pumilus* strain NRRL No. B-30087 and *Ulocladium oudemansii.*

Accordingly, the present invention furthermore relates to compositions comprising one microorganism (I) (component 1) and one further active substance (component 2), which further active substance is selected from the column "Component 2" of the lines B-1 to B-247 of Table B.

A further embodiment relates to the compositions B-1 to B-247 listed in Table B, where a row of Table B corresponds in each case to a fungicidal composition comprising one of the in the present specification individualized compounds of formula I (component 1) and the respective further active substance from groups A) to I) (component 2) stated in the row in question. Preferably, the compositions described comprise the active substances in synergistically effective amounts.

TABLE B

Composition comprising one indiviualized microorganism (I) (*Penicillium bilaji*) and one further active substance from groups A) to F)

| Mixture | Component 1 | Component 2 |
|---|---|---|
| B-1 | *Penicillium bilaji* | Azoxystrobin |
| B-2 | *Penicillium bilaji* | Coumethoxystrobin |
| B-3 | *Penicillium bilaji* | Coumoxystrobin |
| B-4 | *Penicillium bilaji* | Dimoxystrobin |
| B-5 | *Penicillium bilaji* | Enestroburin |
| B-6 | *Penicillium bilaji* | Fluoxastrobin |
| B-7 | *Penicillium bilaji* | Kresoxim-methyl |
| B-8 | *Penicillium bilaji* | Metominostrobin |
| B-9 | *Penicillium bilaji* | Orysastrobin |
| B-10 | *Penicillium bilaji* | Picoxystrobin |
| B-11 | *Penicillium bilaji* | Pyraclostrobin |
| B-12 | *Penicillium bilaji* | Pyrametostrobin |
| B-13 | *Penicillium bilaji* | Pyraoxystrobin |
| B-14 | *Penicillium bilaji* | Pyribencarb |
| B-15 | *Penicillium bilaji* | Trifloxystrobin |
| B-16 | *Penicillium bilaji* | 2-[2-(2,5-dimethyl-phenoxymethyl)-phenyl]-3-methoxy-acrylic acid methyl ester |
| B-17 | *Penicillium bilaji* | 2-(2-(3-(2,6-dichlorophenyl)-1-methyl-allylideneaminooxymethyl)-phenyl)-2-methoxyimino-N-methyl-acetamide |
| B-18 | *Penicillium bilaji* | Benalaxyl |
| B-19 | *Penicillium bilaji* | Benalaxyl-M |
| B-20 | *Penicillium bilaji* | Benodanil |
| B-21 | *Penicillium bilaji* | Bixafen |
| B-22 | *Penicillium bilaji* | Boscalid |
| B-23 | *Penicillium bilaji* | Carboxin |
| B-24 | *Penicillium bilaji* | Fenfuram |
| B-25 | *Penicillium bilaji* | Fenhexamid |
| B-26 | *Penicillium bilaji* | Flutolanil |
| B-27 | *Penicillium bilaji* | Fluxapyroxad |
| B-28 | *Penicillium bilaji* | Furametpyr |
| B-29 | *Penicillium bilaji* | Isopyrazam |
| B-30 | *Penicillium bilaji* | Isotianil |
| B-31 | *Penicillium bilaji* | Kiralaxyl |
| B-32 | *Penicillium bilaji* | Mepronil |
| B-33 | *Penicillium bilaji* | Metalaxyl |
| B-34 | *Penicillium bilaji* | Metalaxyl-M |
| B-35 | *Penicillium bilaji* | Ofurace |
| B-36 | *Penicillium bilaji* | Oxadixyl |
| B-37 | *Penicillium bilaji* | Oxycarboxin |
| B-38 | *Penicillium bilaji* | Penflufen |
| B-39 | *Penicillium bilaji* | Penthiopyrad |
| B-40 | *Penicillium bilaji* | Sedaxane |
| B-41 | *Penicillium bilaji* | Tecloftalam |
| B-42 | *Penicillium bilaji* | Thifluzamide |
| B-43 | *Penicillium bilaji* | Tiadinil |
| B-44 | *Penicillium bilaji* | 2-Amino-4-methyl-thiazole-5-carboxylic acid anilide |
| B-45 | *Penicillium bilaji* | N-(4'-trifluoromethylthiobiphenyl-2-yl)-3-difluoromethyl-1-methyl-1H-pyrazole-4-carboxamide |
| B-46 | *Penicillium bilaji* | N-(2-(1,3,3-trimethyl-butyl)-phenyl)-1,3-dimethyl-5-fluoro-1H-pyrazole-4-carboxamide |

TABLE B-continued

| Composition comprising one indiviualized microorganism (I) (*Penicillium bilaji*) and one further active substance from groups A) to F) | | |
|---|---|---|
| Mixture | Component 1 | Component 2 |
| B-47 | *Penicillium bilaji* | Dimethomorph |
| B-48 | *Penicillium bilaji* | Flumorph |
| B-49 | *Penicillium bilaji* | Pyrimorph |
| B-50 | *Penicillium bilaji* | Flumetover |
| B-51 | *Penicillium bilaji* | Fluopicolide |
| B-52 | *Penicillium bilaji* | Fluopyram |
| B-53 | *Penicillium bilaji* | Zoxamide |
| B-54 | *Penicillium bilaji* | Carpropamid |
| B-55 | *Penicillium bilaji* | Diclocymet |
| B-56 | *Penicillium bilaji* | Mandipropamid |
| B-57 | *Penicillium bilaji* | Oxytetracyclin |
| B-58 | *Penicillium bilaji* | Silthiofam |
| B-59 | *Penicillium bilaji* | N-(6-methoxy-pyridin-3-yl) cyclopropanecarboxylic acid amide |
| B-60 | *Penicillium bilaji* | Azaconazole |
| B-61 | *Penicillium bilaji* | Bitertanol |
| B-62 | *Penicillium bilaji* | Bromuconazole |
| B-63 | *Penicillium bilaji* | Cyproconazole |
| B-64 | *Penicillium bilaji* | Difenoconazole |
| B-65 | *Penicillium bilaji* | Diniconazole |
| B-66 | *Penicillium bilaji* | Diniconazole-M |
| B-67 | *Penicillium bilaji* | Epoxiconazole |
| B-68 | *Penicillium bilaji* | Fenbuconazole |
| B-69 | *Penicillium bilaji* | Fluquinconazole |
| B-70 | *Penicillium bilaji* | Flusilazole |
| B-71 | *Penicillium bilaji* | Flutriafol |
| B-72 | *Penicillium bilaji* | Hexaconazol |
| B-73 | *Penicillium bilaji* | Imibenconazole |
| B-74 | *Penicillium bilaji* | Ipconazole |
| B-75 | *Penicillium bilaji* | Metconazole |
| B-76 | *Penicillium bilaji* | Myclobutanil |
| B-77 | *Penicillium bilaji* | Oxpoconazol |
| B-78 | *Penicillium bilaji* | Paclobutrazol |
| B-79 | *Penicillium bilaji* | Penconazole |
| B-80 | *Penicillium bilaji* | Propiconazole |
| B-81 | *Penicillium bilaji* | Prothioconazole |
| B-82 | *Penicillium bilaji* | Simeconazole |
| B-83 | *Penicillium bilaji* | Tebuconazole |
| B-84 | *Penicillium bilaji* | Tetraconazole |
| B-85 | *Penicillium bilaji* | Triadimefon |
| B-86 | *Penicillium bilaji* | Triadimenol |
| B-87 | *Penicillium bilaji* | Triticonazole |
| B-88 | *Penicillium bilaji* | Uniconazole |
| B-89 | *Penicillium bilaji* | Cyazofamid |
| B-90 | *Penicillium bilaji* | Imazalil |
| B-91 | *Penicillium bilaji* | Imazalil-sulfate |
| B-92 | *Penicillium bilaji* | Pefurazoate |
| B-93 | *Penicillium bilaji* | Prochloraz |
| B-94 | *Penicillium bilaji* | Triflumizole |
| B-95 | *Penicillium bilaji* | Fluazinam |
| B-96 | *Penicillium bilaji* | Pyrifenox |
| B-97 | *Penicillium bilaji* | 3-[5-(4-Chloro-phenyl)-2,3-dimethyl-isoxazolidin-3-yl]-pyridine |
| B-98 | *Penicillium bilaji* | 3-[5-(4-Methyl-phenyl)-2,3-dimethyl-isoxazolidin-3-yl]-pyridine |
| B-99 | *Penicillium bilaji* | Bupirimate |
| B-100 | *Penicillium bilaji* | Cyprodinil |
| B-101 | *Penicillium bilaji* | Diflumetorim |
| B-102 | *Penicillium bilaji* | Fenarimol |
| B-103 | *Penicillium bilaji* | Ferimzone |
| B-104 | *Penicillium bilaji* | Mepanipyrim |
| B-105 | *Penicillium bilaji* | Nitrapyrin |
| B-106 | *Penicillium bilaji* | Nuarimol |
| B-107 | *Penicillium bilaji* | Pyrimethanil |
| B-108 | *Penicillium bilaji* | Triforine |
| B-109 | *Penicillium bilaji* | Fenpiclonil |
| B-110 | *Penicillium bilaji* | Fludioxonil |
| B-111 | *Penicillium bilaji* | Aldimorph |
| B-112 | *Penicillium bilaji* | Dodemorph |
| B-113 | *Penicillium bilaji* | Dodemorph-acetate |
| B-114 | *Penicillium bilaji* | Fenpropimorph |
| B-115 | *Penicillium bilaji* | Tridemorph |
| B-116 | *Penicillium bilaji* | Fenpropidin |
| B-117 | *Penicillium bilaji* | Fluoroimid |
| B-118 | *Penicillium bilaji* | Iprodione |

TABLE B-continued

| Composition comprising one indiviualized microorganism (I) (*Penicillium bilaji*) and one further active substance from groups A) to F) | | |
|---|---|---|
| Mixture | Component 1 | Component 2 |
| B-119 | *Penicillium bilaji* | Procymidone |
| B-120 | *Penicillium bilaji* | Vinclozolin |
| B-121 | *Penicillium bilaji* | Famoxadone |
| B-122 | *Penicillium bilaji* | Fenamidone |
| B-123 | *Penicillium bilaji* | Flutianil |
| B-124 | *Penicillium bilaji* | Octhilinone |
| B-125 | *Penicillium bilaji* | Probenazole |
| B-126 | *Penicillium bilaji* | 5-Amino-2-iso-propyl-4-ortho-tolyl-2,3-dihydro-pyrazole-1-carbothioic acid S-allyl ester |
| B-127 | *Penicillium bilaji* | Acibenzolar-S-methyl |
| B-128 | *Penicillium bilaji* | Ametoctradin |
| B-129 | *Penicillium bilaji* | Amisulbrom |
| B-130 | *Penicillium bilaji* | Anilazin |
| B-131 | *Penicillium bilaji* | Blasticidin-S |
| B-132 | *Penicillium bilaji* | Captafol |
| B-133 | *Penicillium bilaji* | Captan |
| B-134 | *Penicillium bilaji* | Chinomethionat |
| B-135 | *Penicillium bilaji* | Dazomet |
| B-136 | *Penicillium bilaji* | Debacarb |
| B-137 | *Penicillium bilaji* | Diclomezine |
| B-138 | *Penicillium bilaji* | Difenzoquat, |
| B-139 | *Penicillium bilaji* | Difenzoquat-methylsulfate |
| B-140 | *Penicillium bilaji* | Fenoxanil |
| B-141 | *Penicillium bilaji* | Folpet |
| B-142 | *Penicillium bilaji* | Oxolinsäure |
| B-143 | *Penicillium bilaji* | Piperalin |
| B-144 | *Penicillium bilaji* | Proquinazid |
| B-145 | *Penicillium bilaji* | Pyroquilon |
| B-146 | *Penicillium bilaji* | Quinoxyfen |
| B-147 | *Penicillium bilaji* | Triazoxid |
| B-148 | *Penicillium bilaji* | Tricyclazole |
| B-149 | *Penicillium bilaji* | 2-Butoxy-6-iodo-3-propyl-chromen-4-one |
| B-150 | *Penicillium bilaji* | 5-Chloro-1-(4,6-dimethoxy-pyrimidin-2-yl)-2-methyl-1H-benzoimidazole |
| B-151 | *Penicillium bilaji* | 5-Chloro-7-(4-methyl-piperidin-1-yl)-6-(2,4,6-trifluoro-phenyl)-[1,2,4]triazolo[1,5-a]pyrimidine |
| B-152 | *Penicillium bilaji* | 5-Ethyl-6-octyl-[1,2,4]triazolo[1,5-a]pyrimidin-7-yl-amine |
| B-153 | *Penicillium bilaji* | Dodine |
| B-154 | *Penicillium bilaji* | Dodine free base |
| B-155 | *Penicillium bilaji* | Guazatine |
| B-156 | *Penicillium bilaji* | Guazatine-acetate |
| B-157 | *Penicillium bilaji* | Iminoctadine |
| B-158 | *Penicillium bilaji* | Iminoctadine-triacetate |
| B-159 | *Penicillium bilaji* | Iminoctadine-tris(albesilate) |
| B-160 | *Penicillium bilaji* | Kasugamycin |
| B-161 | *Penicillium bilaji* | Kasugamycin-hydrochloride-hydrate |
| B-162 | *Penicillium bilaji* | Polyoxine |
| B-163 | *Penicillium bilaji* | Streptomycin |
| B-164 | *Penicillium bilaji* | Validamycin A |
| B-165 | *Penicillium bilaji* | Binapacryl |
| B-166 | *Penicillium bilaji* | Dicloran |
| B-167 | *Penicillium bilaji* | Dinobuton |
| B-168 | *Penicillium bilaji* | Dinocap |
| B-169 | *Penicillium bilaji* | Nitrothal-isopropyl |
| B-170 | *Penicillium bilaji* | Tecnazen |
| B-171 | *Penicillium bilaji* | Fentin salts |
| B-172 | *Penicillium bilaji* | Dithianon |
| B-173 | *Penicillium bilaji* | Isoprothiolane |
| B-174 | *Penicillium bilaji* | Edifenphos |
| B-175 | *Penicillium bilaji* | Fosetyl, Fosetyl-aluminium |
| B-176 | *Penicillium bilaji* | Iprobenfos |
| B-177 | *Penicillium bilaji* | Phosphorous acid ($H_3PO_3$) and derivatives |
| B-178 | *Penicillium bilaji* | Pyrazophos |
| B-179 | *Penicillium bilaji* | Tolclofos-methyl |
| B-180 | *Penicillium bilaji* | Chlorothalonil |
| B-181 | *Penicillium bilaji* | Dichlofluanid |
| B-182 | *Penicillium bilaji* | Dichlorophen |
| B-183 | *Penicillium bilaji* | Flusulfamide |
| B-184 | *Penicillium bilaji* | Hexachlorbenzene |
| B-185 | *Penicillium bilaji* | Pencycuron |
| B-186 | *Penicillium bilaji* | Pentachlorophenol and salts |
| B-187 | *Penicillium bilaji* | Phthalide |

TABLE B-continued

| Composition comprising one indiviualized microorganism (I) (*Penicillium bilaji*) and one further active substance from groups A) to F) | | |
|---|---|---|
| Mixture | Component 1 | Component 2 |
| B-188 | *Penicillium bilaji* | Quintozene |
| B-189 | *Penicillium bilaji* | Thiophanate Methyl |
| B-190 | *Penicillium bilaji* | Tolylfluanid |
| B-191 | *Penicillium bilaji* | N-(4-chloro-2-nitro-phenyl)-N-ethyl-4-methyl-benzenesulfonamide |
| B-192 | *Penicillium bilaji* | Bordeaux mixture |
| B-193 | *Penicillium bilaji* | Copper acetate |
| B-194 | *Penicillium bilaji* | Copper hydroxide |
| B-195 | *Penicillium bilaji* | Copper oxychloride |
| B-196 | *Penicillium bilaji* | basic Copper sulfate |
| B-197 | *Penicillium bilaji* | Sulfur |
| B-198 | *Penicillium bilaji* | *Bacillus subtilis* NRRL No. B-21661 |
| B-199 | *Penicillium bilaji* | *Bacillus pumilus* NRRL No. B-30087 |
| B-200 | *Penicillium bilaji* | *Ulocladium oudemansii* |

The fungicidal action of the compositions according to the invention can be shown by the tests described below.

The active components, separately or jointly, are prepared as a stock solution comprising 25 mg of active component which is made up to 10 ml using a mixture of acetone and/or DMSO and the emulsifier Uniperol® EL (wetting agent having an emulsifying and dispersing action based on ethoxylated alkylphenols) in a ratio by volume of solvent/emulsifier of 99:1. The mixture is then made up to 100 ml with water. This stock solution is diluted with the solvent/emulsifier/water mixture described to give the concentration stated below.

The visually determined percentages of infected leaf areas are converted into efficacies in % of the untreated control.

The efficacy (E) is calculated as follows using Abbot's formula:

$$E=(1-\alpha/\beta)\cdot 100$$

α corresponds to the fungicidal infection of the treated plants in % and

β corresponds to the fungicidal infection of the untreated (control) plants in %

An efficacy of 0 means that the infection level of the treated plants corresponds to that of the untreated control plants; an efficacy of 100 means that the treated plants were not infected.

The expected efficacies of active compound combinations were determined using Colby's formula (Colby, S. R. "Calculating synergistic and antagonistic responses of herbicide combinations", Weeds, 15, pp. 20-22, 1967) and compared with the observed efficacies.

$$E=x+y-x\cdot y/100 \qquad \text{Colby's formula}$$

E expected efficacy, expressed in % of the untreated control, when using the mixture of the active compounds A and B at the concentrations a and b x efficacy, expressed in % of the untreated control, when using the active compound A at the concentration a y efficacy, expressed in % of the untreated control, when using the active compound B at the concentration b.

The invention claimed is:

1. A fungicidal composition, comprising as active components 1) a microorganism (I) of species *Penicillium bilaji;* and 2) one compound (II) selected from the group consisting of:

A) a strobilurin selected from the group consisting of azoxystrobin, fluoxastrobin, pyraclostrobin, and trifloxystrobin;

B) a carboxamide selected from the group consisting of a carboxanilides selected from the group consisting of bixafen, boscalid, fluxapyroxad, isopyrazam, metalaxyl, metalaxyl-M (mefenoxam), penflufen, penthiopyrad, and sedaxane;

C) an azole selected from the group consisting of cyproconazole, difenoconazole, diniconazole, epoxiconazole, fluquinconazole, ipconazole, metconazole, prothioconazole, tebuconazole triticonazole, imazalil and prochloraz; and D) a heterocyclic compound selected from the group consisting of a pyrimidine selected from the group consisting of bupirimate, cyprodinil, diflumetorim, fenarimol, ferimzone, mepanipyrim, nitrapyrin, nuarimol, and pyrimethanil;

a pyrrole selected from the group consisting of fenpiclonil and fludioxonil;

wherein the microorganism (I) and the one compound (II) are in a synergistically effective amount.

2. The composition of claim 1, wherein the one compound (II) is selected from the group consisting of pyraclostrobin, trifloxystrobin, azoxystrobin and fluoxastrobin.

3. The composition of claim 1, wherein the one compound (II) is selected from the group consisting of boscalid, isopyrazam, metalaxyl, metalaxyl-M, penflufen, penthiopyrad, sedaxane, bixafen and fluxapyroxad.

4. The composition of claim 3, wherein the one compound (II) is selected from the group consisting of penflufen, sedaxane, bixafen and fluxapyroxad.

5. The composition of claim 1, wherein the one compound (II) is selected from the group consisting of cyproconazole, difenoconazole, diniconazole, epoxiconazole, fluquinconazole, metconazole, ipconazole, imazalil, tebuconazole, triticonazole,-prothioconazole, and prochloraz.

6. The composition of claim 5, wherein the one compound (II) is selected from the group consisting of tebuconazole, prothioconazole, triticonazole and prochloraz.

7. The composition of claim 1, wherein the one compound (II) is selected from the group consisting of fludioxonil, cyprodinil, and pyrimethanil.

8. The composition of claim 1, wherein the microorganism (I) and the one compound (II) are present in a weight ratio of from 100:1 to 1:100.

9. The composition of claim 1, further comprising a solvent or solid carrier.

10. A method for controlling phytopathogenic harmful fungi, comprising treating the fungi, their habitat or the seed, the soil or the plants to be protected against fungal attack with an effective amount of the composition of claim 1.

11. The method of claim 10, wherein the one compound (II) is selected from the group consisting of pyraclostrobin, trifloxystrobin, azoxystrobin and fluoxastrobin.

12. The method of claim 10, wherein the one compound (II) is selected from the group consisting of boscalid, isopyrazam, metalaxyl, metalaxyl-M, penflufen, penthiopyrad, sedaxane, bixafen and fluxapyroxad.

13. The method of claim 12, wherein the one compound (II) is selected from the group consisting of penflufen, sedaxane, bixafen and fluxapyroxad.

14. A method for protection of plant propagation material from plant-pathogenic fungi comprising contacting the plant propagation materials with the composition of claim 1 in an effective amount.

15. The method of claim 14, wherein the one compound (II) is selected from the group consisting of pyraclostrobin, trifloxystrobin, azoxystrobin and fluoxastrobin.

16. The method of claim 14, wherein the one compound (II) is selected from the group consisting of boscalid, isopyrazam, metalaxyl, metalaxyl-M, penflufen, dimethomoprh, fluopyram, penthiopyrad, sedaxane, bixafen and fluxapyroxad.

17. The method of claim 14, wherein the microorganism (I) and the one compound (II) are applied simultaneously, that is jointly or separately, or in succession.

* * * * *